Figure 1:
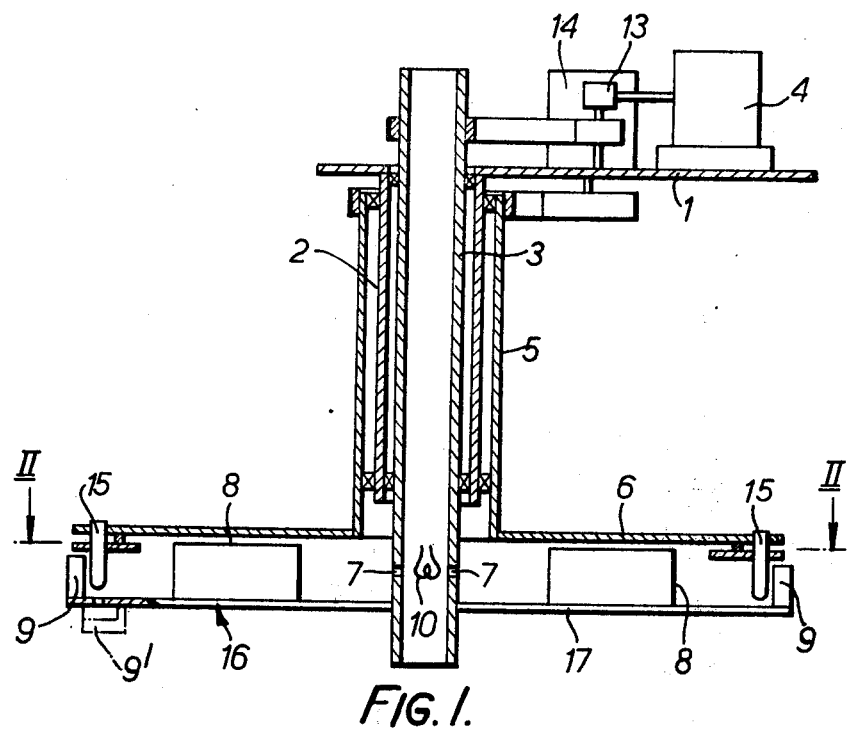

United States Patent [19] [11] 4,412,742
Lloyd [45] Nov. 1, 1983

[54] APPARATUS FOR USE IN INVESTIGATING SPECIMENS
[75] Inventor: Peter H. Lloyd, Birmingham, England
[73] Assignee: National Research Development Corporation, London, England
[21] Appl. No.: 963,938
[22] Filed: Nov. 21, 1978

Related U.S. Application Data
[63] Continuation of Ser. No. 710,556, Aug. 2, 1976, abandoned.

[30] Foreign Application Priority Data
Aug. 8, 1975 [GB] United Kingdom ............... 33250/75
[51] Int. Cl.³ ...................... G01N 21/01; G01N 21/13
[52] U.S. Cl. ..................................... 356/73; 356/244; 422/64
[58] Field of Search .................. 356/39, 73, 206, 244, 356/246, 440; 250/576, 236; 23/259, 291–292; 422/64

[56] References Cited
U.S. PATENT DOCUMENTS

| 978,644 | 12/1910 | Raabe | 422/64 |
|---|---|---|---|
| 1,776,298 | 9/1930 | Strange | 250/236 |
| 3,345,460 | 10/1967 | Betts et al. | 250/236 |
| 3,503,683 | 3/1970 | Isreeli et al. | |
| 3,554,654 | 1/1971 | Paatzsch et al. | |
| 3,748,044 | 7/1973 | Liston | 23/253 |
| 3,829,221 | 8/1974 | de Mendez et al. | 356/440 |
| 3,833,304 | 9/1974 | Liston | |
| 3,834,821 | 9/1974 | Ferrari | 356/246 |
| 3,873,273 | 3/1975 | Moran et al. | 356/246 |
| 3,882,318 | 5/1975 | Mioduski | 250/576 |
| 3,966,322 | 6/1976 | Greaves et al. | 356/39 |
| 4,007,011 | 2/1977 | Greaves et al. | 422/64 |

FOREIGN PATENT DOCUMENTS
100823 4/1937 Australia .
2250986 6/1975 France .
1501883 2/1978 United Kingdom .

OTHER PUBLICATIONS
Anderson, N. G., "Analytical Techniques for Cell Fractions XII A Multiple-Covet Rotor for a New Microanalytical System", Analytical Chem. 28, 1969, pp. 545–562.

Primary Examiner—William H. Punter
Attorney, Agent, or Firm—Cushman, Darby & Cushman

[57] ABSTRACT
The apparatus comprises a circular turntable mounted with its axis of rotation vertical and carrying at respective positions spaced around the peripheral region of the turntable a plurality of specimen containing vials. The turntable is driven by a stepping motor.

A rotor assembly is mounted coaxially with the turntable and comprises a central hollow shaft and a number of arms projecting radially from the shaft. A lamp is situated within the hollow shaft and, by virtue of apertures in the wall of the shaft opposite the lamp, produces radial beams of light which are received by respective receivers on the arms of the rotor assembly, after having been directly transmitted through, or scattered by, the specimens in the vials as the rotor assembly rotates. The output signals from the receivers, which depend upon the intensity of received light, enable the specimens to be investigated.

Preferably, the apparatus is used in the analysis of blood specimens.

51 Claims, 6 Drawing Figures

APPARATUS FOR USE IN INVESTIGATING SPECIMENS

This is a continuation of application Ser. No. 710,556 filed Aug. 2, 1976, now abandoned.

This invention relates to apparatus for use in investigating specimens.

According to one aspect of the invention there is provided apparatus for use in investigating specimens, comprising a carrier adapted to support a plurality of at least partially radiation-transmissive vessels, each for containing a specimen, means for advancing the carrier stepwise in a predetermined direction, means for scanning the vessels sequentially with each of a number of beams of radiation, at least once for each vessel during each dwell period of the carrier between successive stepwise advancements of the carrier, and radiation receiving means comprising a plurality of radiation receivers arranged to receive radiation leaving the vessels and emanating from respective ones of the beams of radiation and arranged to produce output signals which depend upon the intensity of the received radiation.

According to another aspect of the invention there is provided a method of investigating a plurality of specimens in respective vessels which are at least partially radiation-transmissive and are supported by a carrier, which method comprises the steps of advancing the carrier stepwise in a predetermined direction, scanning the vessels sequentially with each of a number of beams of radiation, at least once for each vessel during each dwell period of the carrier between successive stepwise advancements of the carrier, receiving radiation leaving the vessels and emanating from respective ones of the beams of radiation, and producing output signals which depend upon the intensity of the received radiation.

The beams of radiation may all be of the same wavelength or wavelength band, or, in another arrangement, at least two of the beams have different wavelengths or wavelength bands from one another.

When the apparatus is for use in investigating liquid specimens, it preferably comprises a carrier having a rotational axis and having, or adapted to support, a plurality of at least partially radiation-transmissive vials or other vessels, each for containing a liquid specimen to be investigated, in a circular array centred on the said axis, means for rotating the turntable stepwise in the peripheral direction thereof, a rotor assembly having a plurality of radial arms and mounted coaxially with the turntable, means for rotating the rotor assembly through at least 360° during each dwell period of the turntable, means for producing a plurality of radially outwardly directed beams of radiation, which beams are each associated with a respective said arm and are arranged to co-rotate with said rotor assembly and to be directed at each of the vessels in turn during each revolution of the rotor assembly, a plurality of radiation receivers mounted on the free ends of the arms and each arranged to respond to a different radiation wavelength band and to produce output signals which depend on the intensity of radiation leaving the vessels and emanating from the associated beam of radiation, and computer means for processing said output signals.

Generally, the radiation would be optical. By "optical radiation" is intended to be understood radiation of wavelengths greater than X-rays but less than microwaves, i.e. including infra-red and ultra-violet radiation as well as visible radiation.

Figure 2:
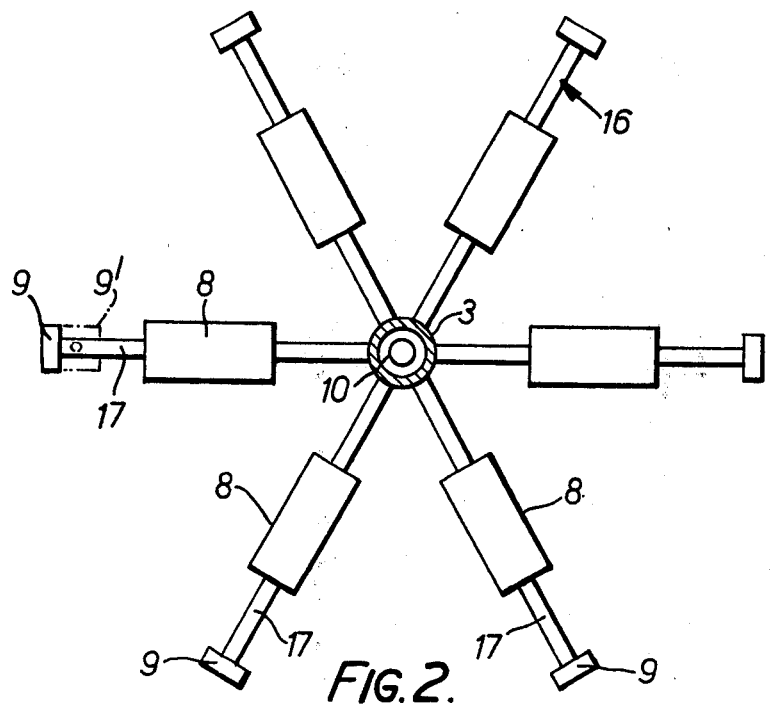
Figure 3:
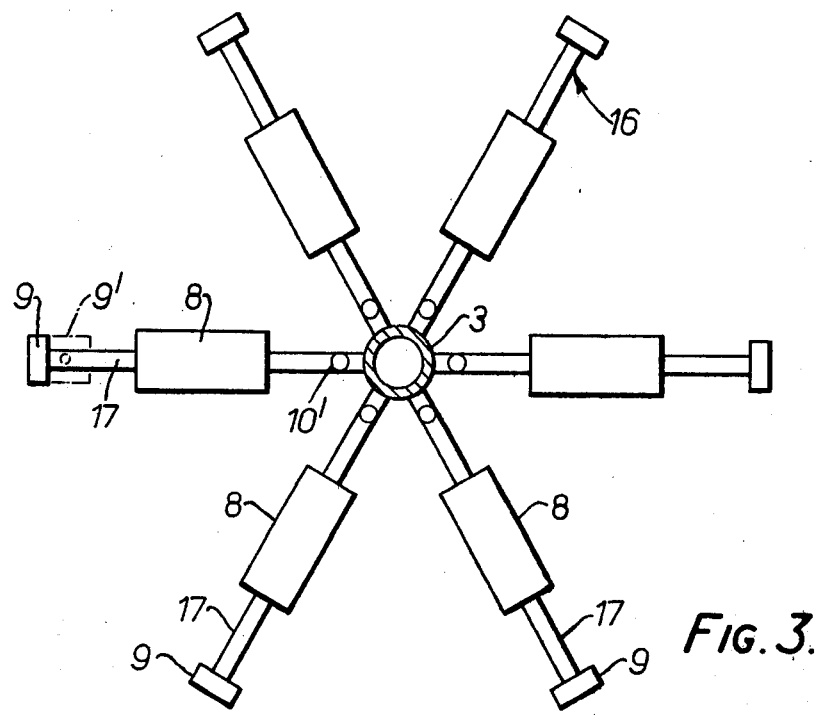
Figure 4:
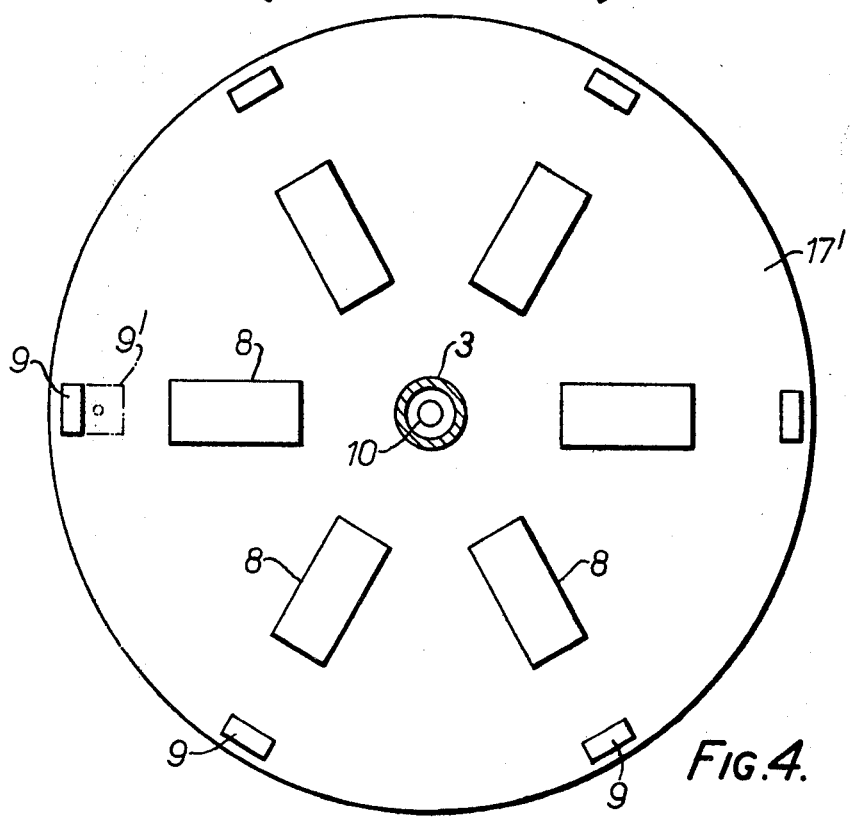
Figure 5:
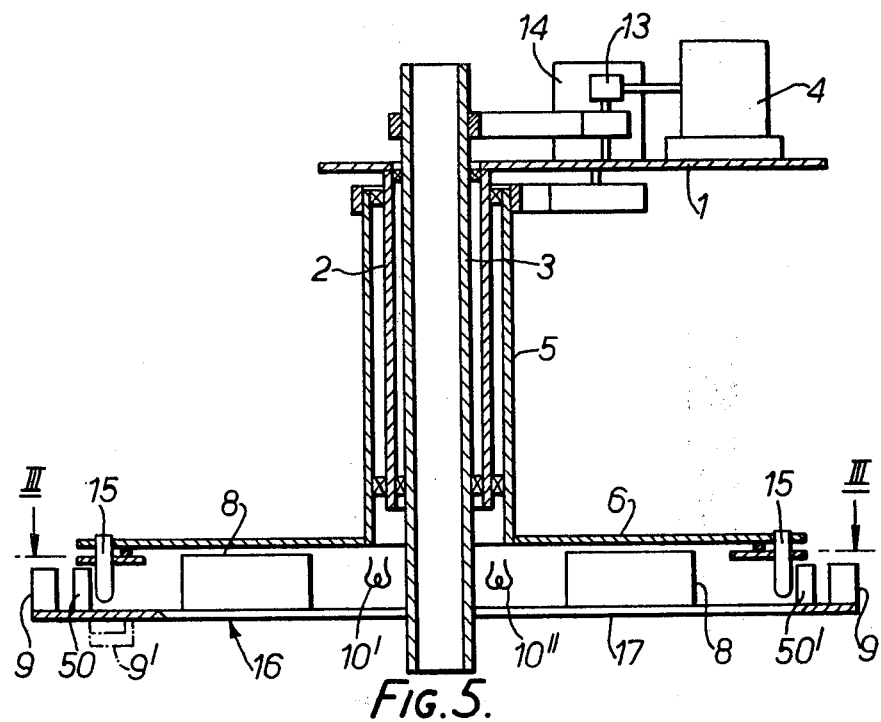
Figure 6:
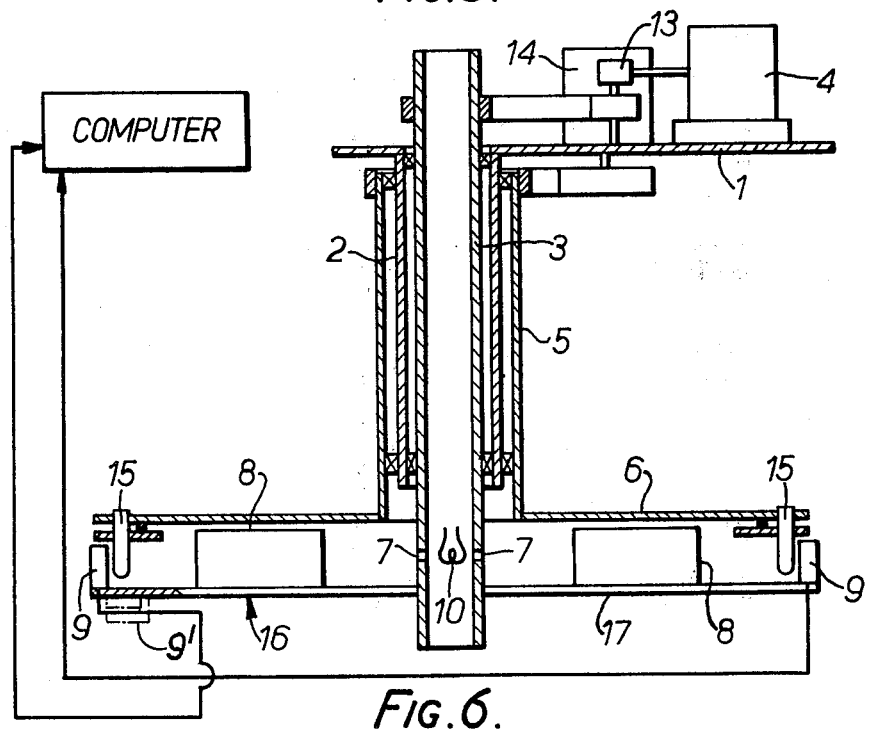

For a better understanding of the invention and to show how the same may be carried into effect, reference will now be made, by way of example, to the accompanying drawings, in which:

FIG. 1 is a vertical sectional view of one form of apparatus in accordance with the invention, forming part of an automatic blood analysing machine, FIG. 2 is a horizontal section showing a rotor assembly of the apparatus, the section being taken along the line II—II of FIG. 1 with a turntable of the apparatus omitted, FIG. 3 is an alternative embodiment in which an assembly of lamps are positioned on the arms of the rotor assembly, FIG. 4 is an alternative embodiment in which the rotor assembly comprises a disc, FIG. 5 is an alternative embodiment in which light sources of different wavelengths are used, and FIG. 6 is a sectional elevation showing a schematic arrangement for electrically connecting the output of a photo-detector and a computer.

The apparatus illustrated in FIGS. 1 and 2 may be used for colorimetric, fluorimetric and turbidimetric evaluation of reactions between samples of blood and reagent(s). The apparatus comprises a stationary frame 1 (of which a part is shown) which carries rotatable shaft support means in the form of a hollow vertical trunnion 2. Extending coaxially inside the trunnion 2 is a hollow rotatable shaft 3 which is connected at its upper end by a pulley and belt arrangement and a gear box 13 to an electric motor 4 mounted on the frame 1. The trunnion 2 is surrounded coaxially by a further hollow rotatable shaft 5 which carries a horizontal carrier or circular turntable 6 near its lower end and is connected near its upper end by a further pulley and belt arrangement to a second electric motor 14, which is a stepping motor for causing a stepping or indexing movement of turntable 6.

The centre of the table 6 is on the common axis of the trunnion 2 and the shafts 3 and 5, and the table 6 has about its periphery a plurality of equally-spaced vials 15 which may also be called cuvettes or vessels. These vials may be fixed relative to the table 6 but they are preferably removably fitted into notches in the table. Each vial extends downwardly from the level of the table into the interior of the frame 1.

The shaft 3 forms part of a second or photometer carrier in the form of a rotor which also comprises a rotor assembly 16 carried by the shaft 3. This assembly, as is clearly shown in FIG. 2, comprises six arms 17 fixedly mounted on the shaft 3 for co-rotation therewith. It could, though, comprise a circular disc 17' as shown in FIG. 4.

The apparatus incorporates an optical system or photometer means comprising a lamp 10, which is mounted on the common axis of the trunnion 2 and the shafts 3 and 5 for co-rotation with the shaft 3, six equally spaced apertures 7 through the wall of the shaft 3, these apertures being opposite the lamp 10 and providing, in use, six light beams which are above, and parallel to, the arms 17 respectively, six optical devices 8 respectively arranged on the arms 17, and six photodetectors 9 respectively mounted at the free ends of the arms and each forming part of an individual photometer. As can be seen from FIGS. 1 and 2, the vials 15 are arranged in the light paths of the various light beams. Each optical device 8 serves to focus its light beam on the vials 15 as they become positioned in the light path of the light beam and will generally include lenses for effecting such focusing. The photodetectors 9 are generally radiant energy or radiation detectors such as photomultiplier tubes or solid-state detectors and are provided with different optical filters so that each photodetector is arranged to respond to a different optical wavelength or wavelength band. As is apparent, each light beam from lamp 10 to the scanned vials 15 has a rectilinear axis, and the light leaving each scanned vial travels rectilinearly to a detector 9.

Finally, the arrangement of the apparatus is such that during each dwell period of the table 6 between successive stepwise advancements of this table, effected by the stepping motor 14, motor 4 drives the rotor assembly through at least 360° of rotation.

When the blood analysing machine is in operation the table 6 is rotated stepwise by the motor 14 past a dispensing station (not shown) at which a sample of blood and a quantity of reagent (and possibly also diluent and/or dye) are placed in a different vial during each dwell period of the table 6 between successive stepwise rotational advancements of the table. At the same time, the motor 4 rotates the shaft 3 through at least one revolution during each dwell period thus causing the arm 17 to rotate so that each of the six beams of radiation is directed at least once at each of the vials. The light transmitted by the liquids in the vials is received by the photodetectors 9 which provide respective output voltages each time that transmitted light is received. The magnitude of the output voltages depends upon the intensity of light received from the vials. The photodetectors are connected to a computer (FIG. 6) which stores data representing the output voltages of the photodetectors. In practice, it is more convenient to rotate the motor continuously rather than for it to rotate only during each dwell period of the table 6. Then, the computer is arranged so as to sample data only during the dwell periods. Furthermore, the computer is preferably so arranged that if during dwell periods the shaft 3 rotates through a non-integral number of revolutions, the computer accepts data only for the nearest integral number of revolutions of the shaft, below the actual number of revolutions undergone.

In the circumstances, therefore, the illustrated apparatus is used for colorimetric analysis of the blood samples. By making a slight modification, however, the apparatus may be used for light-scattering or fluorimetric analysis of the blood samples. The modification is shown in broken lines in FIG. 1 and entails replacing at least one photodetector 9 by a similar photodetector 9' whose input end is vertically below the vial and perpendicular to the path of the light beam directed towards the vial. A different colour filter 50, 50' in FIG. 5 is included in each photodetector 9', so that the output voltage of the photodetector depends on the intensity with which light from the incident light beam in a selected wavelength or wavelength band, predetermined by the filter, is scattered.

In a modification, the lamp 10 is replaced by another lamp arranged on the axis of the shaft 3 near its top end and fixed relative to the shaft 3. By the use of suitable fibre-optic light guides which co-rotate with the shaft 3, light from the lamp is directed, in use, downwardly along the common axis of the trunnion 2 and shafts 3 and 5, and then radially outwardly into the inlets of the various optical devices 8. In another arrangement, the optical devices could be positioned radially outwardly from the vials 15 and suitable fibre-optic light guides provided so as to direct the optical radiation emitted by the lamp at the vials in the radially inward direction, the photodetectors 9 being arranged to receive the transmitted light from the vials. For light-scattering a fluorimetric analysis, however, the position of the photodetectors 9' would be the same as that illustrated in FIG. 1.

The lamp could be positioned near the lower end of the shaft 3 and again provided with suitable fibre-optic guides. Alternatively, each photodetector 9 or 9' could be mounted on its respective arm at a position nearer the axis of the shaft, for example at a position immediately beneath the respective arm and adjacent the outer peripheral surface of the shaft 3, in which case the fibre-optic light guides would extend over the full length of the arms 17 and have their free ends directed radially inwardly. The light guides may be replaced by a suitable system of mirrors or prisms. Although it is preferred for a single lamp to be employed in the optical system, it would, alternatively, be possible for the apparatus to include an assembly of lamps 10', 10" (FIG. 5) for the respective arms of the rotor assembly as shown in FIG. 3.

If the lamps 10', 10" all emit optical radiation in the same wavelength band, the photodetectors respond to different wavelengths or wavelength bands included within the wavelength band of the emitted optical radiation. In another arrangement, the lamps emit optical radiation at respective wavelengths or in respective wavelength bands, in which case each photodetector is adapted to respond to the wavelength or wavelength band of its respective lamp or it may respond to a wider wavelength band. Whatever arrangement is employed, data for each vial at the various wavelengths or wavelength bands in question is obtained for each revolution of the rotor assembly 16.

The wavelength or wavelength band of the beams of emitted radiation and of the photodetectors may all be identical, in which case six sets of data are obtained for each revolution of the rotor assembly so that a mean value for each vial may be determined.

Although it is preferred for each photodetector to respond to a different wavelength or wavelength band, it is alternatively possible for, for example, three of the photodetectors to respond to one band and the other three to respond to another band. Then, the mean value of the output voltages of the photodetectors responding to either wavelength band can be obtained for greater accuracy.

I claim:

1. Apparatus for monitoring chemical reactions occurring in a plurality of liquid or like sample substances carried in a plurality of respective cuvettes whose walls are at least to some extent capable of transmitting radiant energy which comprises:

support means, a rotor mounted on said support means for rotation thereon on an axis, a turntable mounted coaxially with the rotor for rotation relative to said support means, and for holding a plurality of said radiant-energy-transmissive cuvettes in a circular arrangement coaxially with said axis, first drive means for rotating the turntable on its axis in a first program of rotation whereby the cuvettes describe an annular path as the turntable rotates.

second drive means for rotating the rotor on said axis in a second program of rotation in which the number of total revolutions of the rotor for a given period of time is greater than the number of revolutions of the turntable for the same period of time, and photometer means including radiant energy source means fixedly mounted on the rotor for rotation therewith and defining at least one beam path for radiant energy from said source means which extends at least through said annular path such that the beam path includes and traverses at least a portion of the sample substance which may be contained in any of said cuvettes which intersects such beam path during rotation of the turntable, said photometer means including electrical signal production means fixed on the rotor to rotate therewith for responding to any radiant energy projected along said beam path to produce electrical signals as cuvettes intersect said beam path.

2. The apparatus as in claim 1 in which the beam path is arranged radially and normally relative to the said axis and at all times intersects said annular path described by said cuvettes.

3. The apparatus as in claim 1 in which the first drive means rotate the turntable stepwise to provide a moving period and a dwell period for each cuvette relative to a fixed point of the support means.

4. Apparatus as in claim 2 in which the photometer means comprise a source of radiant energy as said source means and at least one radiant energy detector, the beam path being rectilinear from the source to the detector.

5. Apparatus as claimed in claim 1 in which the radiant energy source means comprise a single source at said axis.

6. The apparatus as claimed in claim 1 in which said responding means comprise a plurality of photodetector fixedly mounted on said rotor and circumferentially spaced thereabout, each photodetector having structure defining a beam path for radiant energy disposed radially relative to the axis of the rotor such that all beam paths will extend through said annular path and the cuvettes will intersect all of the beam paths as the rotor rotates, each photodetector including independent means responsive to its radiant energy beam to produce electrical signals as the cuvettes pass through the beam.

7. Apparatus as claimed in claim 6 in which the drive means rotate the turntable stepwise to provide a dwell period and a moving period for each cuvette relative to the support means.

8. Apparatus as claimed in claim 7 in which at least two of the photometers are constructed to be responsive to incident radiant energy at different wavelengths.

9. Chemical reaction monitoring apparatus comprising:

cuvette carrier means, photometer carrier means, a plurality of photometers fixedly mounted on the photometer carrier means and including an electrical signal generating type of radiant energy detector for each photometer and source means of radiant energy also fixedly mounted on the photometer carrier means projecting an energy beam to each said detector, said source means and photometer detectors being thereby fixed relative to each other and to said photometer carrier means for movement therewith, the cuvette carrier means being adapted to carry at least one radiant-energy-transmissive cuvette with a liquid sample contained therein to enable a condition of chemical reaction therein to be monitored, means for moving both the cuvette carrier means and the photometer carrier means in repetitious cycling movements relative to one another so that each beam intersects and passes through said cuvette once each cycle, and means responsive to the outputs of said detectors for acquiring usable data relating to said condition.

10. The apparatus as claimed in claim 9 including a plurality of cuvettes spaced along said cuvette carrier means and wherein each cuvette follows the identical path as the cuvette carrier means moves, each cuvette being intercepted by all of said beams once each cycle.

11. The apparatus as claimed in claim 10 in which the movement of the cuvette carrier means is an indexing movement while the movement of the photometer carrier means is continuous and at a substantially greater speed than that of said cuvette carrier means.

12. Apparatus for use in investigating specimens comprising:

a rotatable carrier having a plurality of holders spacedly disposed on at least one annular path coaxial with said carrier and adapted to support specimen vessels that are at least partially radiation-transmissive;

means for rotating said carrier in a stepwise manner to describe an annular path for said holders and to effect dwell periods between stepwise rotations of said carrier; and means for sequentially scanning at least a predetermined number of said specimen vessels with a multiple of radiation beams between said stepwise rotations of said carrier, the scanning means comprising:

rotatable means mounted coaxially with said carrier and including radiation source means fixedly mounted on said rotatable means to rotate therewith and being disposed centrally of said holders for simultaneously directing a plurality of radiation beams radially across said annular path at a level to intersect specimen vessels when disposed in said holders, a plurality of electrical signal generating type of radiation detector means respectively for said beams fixedly mounted on said rotatable means outside said annular path to rotate with said rotatable means for detecting radiation of the respective beam that has travelled through a specimen vessel held by a said holder for producing respective electrical output signals in response to the intensity of the detected radiation, and means for rotating said rotatable means, source and detector means substantially one complete rotation during each said dwell period of said carrier.

13. Apparatus according to claim 12, wherein said holders are disposed at respective positions substantially equally spaced from the axis of rotation of the carrier and distributed substantially uniformly about said axis.

14. Apparatus according to claim 12, wherein the rotatable means includes a hollow rotatable shaft and said radiation source means includes a radiation source mounted centrally within said hollow rotatable shaft, said shaft having apertures in its wall which are opposite the radiation source so as to produce a number of said radial radiation beams.

15. Apparatus according to claim 12 for use in carrying out colorimetric analysis of a plurality of specimens, wherein each detector means is positioned on said rotatable means with its radiation sensitive part in alignment with, and confronting, the associated beam of radiation so as to receive radiation which is directly transmitted through the specimens in the vessels.

16. Apparatus according to claim 12 for use in carrying out light-scattering or fluorimetric analysis of a plurality of specimens, wherein each detector means is positioned on said rotatable means with its radiation sensitive part directed substantially perpendicularly with respect to the associated beam of radiation so as to receive radiation from the vessels produced by scattering or fluorescence.

17. Apparatus according to claim 12, wherein the beams of radiation are all of the same wavelength or wavelength band.

18. Apparatus according to claim 12, wherein at least two of the beams have different wavelengths or wavelength bands from one another.

19. Apparatus according to claim 18, wherein all the beams have different wavelengths or wavelength bands.

20. Apparatus according to claim 12 said radiation source means produces optical radiation and wherein each detector means comprises:
   a photodetector that is arranged to produce output signals in response to the received intensity of said optical radiation; and
   a color filter arranged on the optical path to the photodetector to prevent optical radiation outside the wavelength band of the filter from reaching the photodetector.

21. Apparatus according to claim 20, wherein at least two of the wavelength bands associated with the filters are different.

22. Apparatus according to claim 21, wherein the wavelength bands associated with the filters are all different.

23. Apparatus according to claim 20, comprising computer means arranged to correlate the output signals from the photodetectors with the instantaneous angular position of the said rotatable means about the axis of rotation thereof.

24. Apparatus for use in investigating specimens comprising:
   a rotatable carrier adapted to support a plurality of specimen vessels that are at least partially radiation-transmissive;
   means for rotating said carrier in a desired manner;
   means for establishing successive periods during operation of said rotating means for investigating said specimens; and
   means for sequentially scanning at least a predetermined number of said specimen vessels with a multiple of optical radiation beams concurrently with operation of said carrier rotating means, the scanning means comprising:
   a rotor comprising a shaft that is mounted coaxially with the carrier,
   a plurality of optical radiation sources fixedly mounted on said rotor and arranged to direct respective radiation beams from said radiation sources towards the specimen vessels,
   a plurality of detector means fixedly mounted on said rotor, each of said detector means corresponding to a respective one of said radiation sources, for separately detecting radiation which has travelled along respective optical paths through said specimen vessels and for producing output signals in response to the intensity of the detected radiation, and
   means for rotating said rotor at least one complete rotation during each of said investigating periods such that each of said radiation beams is directed at desired specimen vessels at least once during each said period.

25. Apparatus as in claim 12, said radiation source means being on substantially the same level as said detector means.

26. Apparatus as in claim 12 or 25 wherein said radiation source means includes respective radiation sources for said plurality of detector means.

27. Apparatus as in claim 12 wherein said rotatable means includes a plurality of radial arms on which said detector means are respectively mounted.

28. Apparatus as in claim 12 wherein said rotatable means includes a disc on which said detector means are mounted.

29. Apparatus for use in investigating specimens, comprising:
   a first carrier adapted to support a plurality of at least partially radiation-transmissive vessels, each for containing a specimen,
   means for advancing the first carrier at least intermittently to effect an overall movement of the first carrier such that supported vessels will in sequence traverse the same predetermined path,
   a second carrier arranged for movement relative to the first carrier,
   a radiation emitting system including at least one radiation source fixedly carried by the second carrier to move therewith,
   means also fixedly carried by the second carrier for forming radiation emitted by said system into at least one beam,
   means for effecting a cyclic movement of the second carrier while said overall movement of the first carrier is being brought about, the cyclic movement being such that said beam will during each cycle sweep along at least a portion of said path within which a plurality of the vessels may be located and such that a plurality of cycles will occur while any given vessel is traversing said portion of said path, and
   detecting means comprising an electrical signal generating type of radiation detector fixedly carried by the second carrier to move therewith for receiving radiation which leaves any specimen contained in one of the vessels as a result of said beam sweeping across that vessel as it sweeps along said portion of said path and generating electrical signals corresponding to the received radiation.

30. Apparatus as in claim 29 wherein said path is endless.

31. Apparatus for use in investigating specimens, comprising:
   a turntable adapted to support a plurality of at least partially radiation-transmissive vessels, each for containing a specimen, at respective positions substantially equally spaced from the axis of rotation of the turntable,
   means for advancing the turntable at least intermittently to effect an overall rotation of the turntable about said axis so that supported vessels will in sequence traverse the same annular path,
   a rotor arranged for rotary movement about said axis relative to the turntable, a radiation emitting system including at least one radiation source fixedly carried by the rotor to rotate therewith, means also fixedly carried by the rotor for forming radiation emitted by said system into at least one beam, means for effecting a cyclic rotary movement of the rotor about said axis while said overall rotation of the turntable is being brought about, the cyclic movement being such that said beam will during each cycle sweep along at least a portion of said path within which a plurality of the vessels may be located and such that a plurality of cycles will occur while any given vessel is traversing said portion of said path, and detecting means comprising an electrical signal generating type of radiation detector fixedly carried by the rotor to rotate therewith for receiving radiation which leaves any specimen contained in one of the vessels as a result of said beam sweeping across that vessel as it sweeps along said portion of said path and generating electrical signals corresponding to the received radiation.

32. Apparatus according to claim 31 in which the radiation emitting system and the beam forming means are arranged so that said beam has a rectilinear axis between the radiation emitting system and said path, and said detector is disposed so so that said radiation which it is arranged to receive is radiation which travels rectilinearly from a specimen contained in one of the vessels.

33. Apparatus according to claim 32 in which the axis of said beam extends radially and perpendicularly with respect to said axis of rotation.

34. Apparatus according to claim 31 in which the beam forming means is arranged to form the radiation emitted by said system into a plurality of separate beams which will intersect said path at different locations, said cyclic movement being such that said beams will during each cycle sweep in turn along said portion of said path, and the detecting means comprises a plurality of radiation detectors fixedly carried by the rotor and respectively corresponding to said beams, each detector being arranged to receive radiation which leaves any specimen contained in one of the vessels as a result of the corresponding beam sweeping across that vessel as it sweeps along said portion of said path.

35. Apparatus according to claim 34 in which at least two of said detectors are respectively arranged to receive radiation of different wavelengths or wavelength bands.

36. Apparatus according to claim 35 in which said wavelengths or wavelength bands are selected by means of filters respectively associated with the detectors.

37. Apparatus according to claim 35 in which at least two of said beams have different wavelengths or wavelength bands from one another.

38. Apparatus according to claim 34 in which the radiation emitting system comprises a single light source disposed centrally with respect to said axis of rotation.

39. Apparatus according to claim 38 in which the light source and the beam forming means are arranged so that each beam has a rectilinear axis between the source and said path.

40. Apparatus according to claim 39 in which the axis of each beam extends radially and perpendicularly with respect to said axis of rotation.

41. Apparatus according to claim 40 in which the light source is mounted within a hollow shaft forming part of the rotor and having an axis coincident with said axis of rotation, the shaft having apertures formed in its wall at positions which are in register with the light source along the length of the shaft.

42. Apparatus according to claim 39, 40 or 41, in which at least one of said detectors is disposed so as to receive directly light which is transmitted through any specimen contained in one of the vessels as a result of the corresponding beam sweeping across that vessel as it sweeps along said portion of said path.

43. Apparatus according to claim 39, 40 or 41, in which at least one of said detectors is disposed so as to receive directly light which travels from any specimen contained on one of the vessels substantially perpendicularly to the axis of the corresponding beam as a result of that beam sweeping across that vessel as it sweeps along said portion of said path.

44. Apparatus according to claim 38 in which each of said detectors is provided with an associated optical filter effective to cause the detector to respond only to light in a selected wavelength band.

45. Apparatus according to claim 44 in which the selected wavelength bands for at least two of said detectors are different from one another.

46. Apparatus according to claim 31 in which the advancing means is operative to effect a stepwise rotation of the turntable.

47. Apparatus according to claim 46 in which the rotor is arranged to rotate about said axis of rotation continuously and unidirectionally at a speed such that at least one complete revolution of the rotor occurs for each step of the turntable rotation.

48. Apparatus according to claim 46 or 47, further comprising means for deriving data from said detecting means only during the dwell periods of the turntable between successive steps of its rotation.

49. Apparatus according to claim 34 in which the advancing means is operative to effect a stepwise rotation of the turntable.

50. Apparatus according to claim 49 in which the rotor is arranged to rotate about said axis of rotation continuously and unidirectionally at a speed such that at least one complete revolution of the rotor occurs for each step of the turntable rotation.

51. Apparatus according to claim 49 or 50, further comprising means for deriving data from said detecting means only during the dwell periods of the turntable between successive steps of its rotation.

* * * * *

UNITED STATES PATENT AND TRADEMARK OFFICE
CERTIFICATE OF CORRECTION

PATENT NO. : 4,412,742
DATED : November 1, 1983
INVENTOR(S) : Peter H. LLOYD

It is certified that error appears in the above—identified patent and that said Letters Patent is hereby corrected as shown below:

Claim 20, column 7, line 22, before "said" insert

--wherein--

Signed and Sealed this

Twenty-second Day of October 1985

[SEAL]

Attest:

Attesting Officer

DONALD J. QUIGG

Commissioner of Patents and Trademarks—Designate